(12) United States Patent
Doudna et al.

(10) Patent No.: US 8,206,968 B2
(45) Date of Patent: *Jun. 26, 2012

(54) MUTANT PROTEINASE WITH REDUCED SELF-CLEAVAGE ACTIVITY AND METHOD OF PURIFICATION

(75) Inventors: Jennifer A. Doudna, Berkeley, CA (US); Louise J. Lucast, Guilford, CT (US); Robert T. Batey, Boulder, CO (US)

(73) Assignee: Yale University, New Haven, CT (US)

( * ) Notice: Subject to any disclaimer, the term of this patent is extended or adjusted under 35 U.S.C. 154(b) by 465 days.

This patent is subject to a terminal disclaimer.

(21) Appl. No.: 12/184,315

(22) Filed: Aug. 1, 2008

(65) Prior Publication Data

US 2008/0318273 A1     Dec. 25, 2008

Related U.S. Application Data

(63) Continuation of application No. 10/343,766, filed as application No. PCT/US01/18620 on Jun. 11, 2001, now Pat. No. 7,494,786.

(60) Provisional application No. 60/211,535, filed on Jun. 15, 2000.

(51) Int. Cl.
    *C12N 9/50*             (2006.01)
(52) U.S. Cl. ...................................... 435/219
(58) Field of Classification Search ........................ None
    See application file for complete search history.

(56) References Cited

U.S. PATENT DOCUMENTS

| 5,532,142 A | 7/1996 | Johnston et al. |
| 2004/0072179 A1 | 4/2004 | Doudna et al. |

OTHER PUBLICATIONS

Carrington J.C. and Dougherty W.G., "A viral cleavage site cassette: identification of amino acid sequences required for tobacco etch virus polyprotein processing," Proc. Natl. Acad. Sci. USA. May 1988; 85(10):3391-5.
Carrington et al., "Internal cleavage and trans-proteolytic activities of the VPg-proteinase (NIa) of tobacco etch potyvirus in vivo," J. Virol. Dec. 1993; 67(12):6995-7000.
Dougherty et al., "Characterization of the catalytic residues of the tobacco etch virus 49-kDa proteinase," Virology, Sep. 1989; 172(1):302-10.
Kapust et al., "The P1' specificity of tobacco etch virus protease," Biochem. Biophys. Res. Commun. Jun. 28, 2002; 294(5):949-55.
Kapust et al., "Tobacco etch virus protease: mechanism of autolysis and rational design of stable mutants with wild-type catalytic proficiency," Protein Eng. Dec. 2001; 14(12):993-1000.
Argos et al. (1984) "Similarity in gene organization and homology between proteins of animal picornaviruses and plant comoviruses suggest common ancestry of these virus families," Nucleic Acids Res. I2(18):7251-7267.
Bazan et al. (1990) "Structural and catalytic models of trypsin-like viral proteases," Semin. Virol. 1:311-322.
Dougherty et al. (1980) "Translation of potyvirus RNA in a rabbit reticulocyte lysate: identification of nuclear inclusion proteins as products of tobacco etch virus RNA translation and cylindrical inclusion protein as a product of the potyvirus genome," Virology 104:174-182.
Dougherty et al. (1988) "Biochemical and mutational analysis of a plant virus polyprotein cleavage site," EMBO J. 7(5):1281-1287.
Dougherty et al. (1989) "Molecular genetic and bio-chemical evidence for the involvement of the heptapeptide cleavage sequence in determining the reaction profile at two tobacco etch virus cleavage sites in cell-free assays," Virology 172(1):145-155.
Dougherty et al. (1989a) "Molecular genetic analysis of a plant virus polyprotein cleavage site: a model," Virology 171 (2):356-364.
Dougherty et al. (1991) "Post-translational processing of the tobacco etch virus 49-kDa small nuclear inclusion polyprotein: identification of an internal cleavage site and delimitation of VPg and proteinase domains," Virology 183:449-456.
Hwang et al. (2000) "Molecular cloning, expression, and purification of nuclear inclusion A protease from tobacco vein mottling virus," Mol. Cells 19(2):148-155.
Krausslich et al. (1988) "Viral proteinases," Annu. Rev. Biochem. 57:701-754.
Lucast et al. (2001) "Large-scale purification of a stable form of recombinant tobacco etch virus protease," BioTechniques 30(3):544-554.
Parks et al. (1994) "Release of proteins and peptides from fusion proteins using a recombinant plant virus proteinase," Anal. Biochem. 216(2):413-417.
Parks et al. (1995) "Expression and purification of a recombinant tobacco etch virus NIa proteinase: biochemical analyses of the full-length and a naturally occurring truncated proteinase form," Virology 210(1 ):194-201.
Polayes et al. (1994) "TEV protease, recombinant: a site-specific protease for efficient cleavage of affinity tags from expressed proteins," Focus 16(1), Life Technologies, Inc.
Yusof et al. (2000) "Purified NS2B/NS3 serine protease of dengue virus type 2 exhibits cofactor NS2B dependence for cleavage of substrates with dibasic amino acids in vitro," J. Biol. Chem. 275(14):9963-9969.
Kim et al., "Expression, Purification, and Identification of a Novel Self-Cleavage Site of the NIa C-Terminal 27-kDa Protease of Turnip Mosaic Potyvirus C5," Virology 213:517-525 (1995).
Lejeune, "International Search Report," from International Patent Application No. PCT/US01/18620, European Patent Office (dated Feb. 2002).

*Primary Examiner* — Nancy Vogel
(74) *Attorney, Agent, or Firm* — Cooley LLP

(57) ABSTRACT

The present invention provides a mutant 27 kDa NIa proteinase having reduced self-cleavage activity relative to the self-cleavage activity of its wild-type proteinase. The mutant has the same substrate cleavage activity as the wild-type proteinase but is more stable than the wild-type proteinase. The present invention also provides a method of obtaining large quantities of active 27 kDa NIa proteinase for use as a tool for purification of other proteins.

2 Claims, 4 Drawing Sheets

| Lane | Sample |
|---|---|
| 1 | TPWT lysate |
| 2 | TPWT soluble fraction |
| 3 | TPWT insoluble fraction (in GuHCl) |
| 4 | TPWT soluble NiNTA-pure |
| 5 | TPWT insoluble NiNTA-pure |
| 6 | GibcoBRL 10kD protein ladder |
| 7 | TPSN lysate |
| 8 | TPSN soluble fraction |
| 9 | TPSN insoluble fraction (in GuHCl) |
| 10 | TPSN soluble NiNTA-pure |
| 11 | TPSN insoluble NiNTA-pure |
| 12 | GibcoBRL 10kD protein ladder |
| 13 | GibcoBRL rTEVP |
| 14 | TPWT (refolded) |
| 15 | TPSN (refolded) |

| Lane | Sample |
|---|---|
| 1 | GibcoBRL rTEVP - 4C |
| 2 | TPWT - 4C |
| 3 | TPSN - 4C |
| 4 | GibcoBRL rTEVP - -20C |
| 5 | TPWT - -20C |
| 6 | TPSN - -20C |
| 7 | GibcoBRL 10kD ladder |
| 8 | GibcoBRL rTEVP - -80C |
| 9 | TPWT - -80C |
| 10 | TPSN - -80C |
| 11 | GibcoBRL 10kD ladder |

SEQUENCE LISTING

```
<160> NUMBER OF SEQ ID NOS: 7

<210> SEQ ID NO 1
<211> LENGTH: 7
<212> TYPE: PRT
<213> ORGANISM: artificial
<220> FEATURE:
<223> OTHER INFORMATION: motif for proteinase active site
<220> FEATURE:
<221> NAME/KEY: MISC_FEATURE
<222> LOCATION: (2)..(7)
<223> OTHER INFORMATION: Xaa at positions 2, 3, and 5 is any amino
      acid; Xaa at position 7 is S or G.

<400> SEQUENCE: 1

Glu Xaa Xaa Tyr Xaa Gln Xaa
1               5

<210> SEQ ID NO 2
<211> LENGTH: 33
<212> TYPE: DNA
<213> ORGANISM: Potyvirus

<400> SEQUENCE: 2
catcagcggg ccatggctga aagcttgttt aag                                33

<210> SEQ ID NO 3
<211> LENGTH: 67
<212> TYPE: DNA
<213> ORGANISM: Potyvirus

<400> SEQUENCE: 3
ctgatgcacg gatcctcatt aatggtgatg gtgatggtgc aattgcgagt agactaattc    60
actcatg                                                             67

<210> SEQ ID NO 4
<211> LENGTH: 66
<212> TYPE: DNA
```

```
<213> ORGANISM: artificial
<220> FEATURE:
<223> OTHER INFORMATION: PCR primer for generating mutant NIa
      proteinase

<400> SEQUENCE: 4
gagttgagtt gcttctttga ctggctgaaa gggttcttca ggtttgttca tgaaaacttt     60
gtggcc                                                                66

<210> SEQ ID NO 5
<211> LENGTH: 7
<212> TYPE: PRT
<213> ORGANISM: Potyvirus

<400> SEQUENCE: 5

Glu Asn Leu Tyr Phe Gln Gly
1               5

<210> SEQ ID NO 6
<211> LENGTH: 4
<212> TYPE: PRT
<213> ORGANISM: artificial
<220> FEATURE:
<223> OTHER INFORMATION: N-terminus of mutant NIa proteinase

<400> SEQUENCE: 6

Met Ala Glu Ser
1

<210> SEQ ID NO 7
<211> LENGTH: 7
<212> TYPE: PRT
<213> ORGANISM: artificial
<220> FEATURE:
<223> OTHER INFORMATION: C-terminus of mutant NIa proteinase

<400> SEQUENCE: 7

Leu His His His His His His
1               5
```

US 8,206,968 B2

MUTANT PROTEINASE WITH REDUCED SELF-CLEAVAGE ACTIVITY AND METHOD OF PURIFICATION

This application is a continuation of U.S. Ser. No. 10/343,766 filed on Oct. 9, 2003, now U.S. Pat. No. 7,494,786, issued on Feb. 24, 2009, which is a 35 U.S.C. 371 application of PCT/US01/18620 filed on Jun. 11, 2001, which claims benefit of U.S. Ser. No. 60/211,535 filed on Jun. 15, 2000. All of these applications are incorporated in their entirety by reference for all purposes.

FIELD OF THE INVENTION

The present invention is related to compositions comprising mutant proteinase having reduced self-cleavage activity relative to the self-cleavage activity of its wild-type proteinase. The mutant proteinase has the same substrate cleavage-activity as its wild-type proteinase and it is more stable than its wild-type proteinase. The present invention is also related to methods of obtaining large quantities of purified active proteins that form inclusion bodies in cells.

BACKGROUND

Proteinases are present in both prokaryotic and eukaryotic systems and have been shown to play an important role in the processing of large precursor polyproteins during viral replication. The reliance of viruses on proteolytic processing by virally encoded proteases has been suggested to have several evolutionary advantages, such as a need for reduced genomic content and partial release from the constraints of the mechanisms of transcriptional and translational regulation of the host cell (Lawson et al., 1990). Viruses have evolved methods for regulating the proteolytic cascade that produces viral structural and replication proteins to replace the host mechanisms. Lawson et al. (1991) report that in picornaviruses, the temporal and spatial distribution of expressed protease activity affects the appearance and location of the final proteolytic product.

Potyviruses are members of the picornaviral superfamily that infect plants. Like other members of the picornaviral family, potyviruses make extensive use of proteinases during replication. An example of a potyvirus that possesses a genome encoding a single large polyprotein proteolytically processed by virally encoded protease is the tobacco etch virus (TEV). TEV has a single-strand, plus-sense RNA genome of about 9,500 nucleotides. The RNA is organized as a single open reading frame and encodes a 346 kDa polyprotein (Allison et al., 1986). The polyprotein is co- and post-translationally processed by viral encoded proteinases. Two proteinases, P1 and helper component proteinase (HC-Pro), are responsible for their autocatalytic release from the amino-terminus of the polyprotein (Verchot et al. 1991; Carrington et al., 1989). The third proteinase, nuclear inclusion proteinase (NIa), mediates all other cleavage events.

Characterization of the 27 kDa NIa Proteinase of Potyvirus

The NIa proteinase is 49 kDa and is found as an aggregate with the 54 kDa NIb polypeptide in nuclear inclusion bodies in infected plant cells (Carrington et al., 1988; Parks et al., 1995). The 49 kDa NIa proteinase is a picornavirus 3C-like proteinase that recognizes cleavage sites within the C-terminal two-thirds of the polyprotein. The proteolytic domain of NIa lies within the C-terminal half of the protein and has a molecular weight of about 27 kDa, while the N-terminal region of NIa contains the Vpg (viral protein, genome-linked) activity and has a molecular weight of about 21 kDa.

Structurally, the 27 kDa NIa proteinase has been reported to be similar to the trypsin-like family of cellular serine proteinases, such as chymotrypsin or trypsin, with the substitution of Cys for serine as the active site nucleophile (Blazan et al., 1990; Dougherty et al., 1989). Dougherty et al. (1989) disclose that the catalytic triad of 27 kDa proteinase is composed of His, Asp, and Cys, being similar to the catalytic triad found in other viral proteinases (Dougherty et al., 1989). However, unlike the other proteinases, the 27 kDa proteinase recognizes an extended heptapeptide sequence, E-X-X-Y-X-Q↓S/G (positions P6-P1↓P'1; X is any amino acid) (SEQ ID NO: 1), and cleaves within the heptapeptide sequence (Dougherty et al., 1989a; Dougherty et al., 1988; Dougherty et al., 1989b). Residues at positions P6, P3, P1, and P'1 are conserved and essential for optimal cleavage. Amino acids at the other positions appear to modulate the rate at which cleavage occurs (Dougherty et al., 1989; Dougherty and Parks, 1989).

Moreover, the 27 kDa NIa proteinase appears to be structurally and functionally similar to other plus-stranded RNA viral-encoded proteinases (Krausslich and Wimmer, 1998). First of all, it cleaves the polyprotein between particular Gln-Gly or Glyn-Ser dipeptides. Secondly, proteolytic activity is enhanced by dithiothreitol. Thirdly, the gene encoding this proteinase is adjacent to the putative RNA-dependent, RNA-polymerase gene. Lastly, the proteinase contains a conserved C-terminal amino acid motif (Cys-~15 amino acids-His) (Argos et al., 1984). This last characteristic is shared by proteinases encoded by many RNA viruses that translationally express their genetic information as a single polyprotein from genome length RNA (Dougherty et al., 1989).

Additionally, Parks et al (1995) report that the 27 kDa NIa proteinase contains an internal self-cleavage site positioned at 24 amino acids from the carboxyl terminus of the proteinase and that the active 27 kDa proteinase converts to a lower molecular weight form with time. The 27 kDa NIa proteinase lacking the C-terminal 24 amino acids exhibits limited activity. The truncated proteinase is about one-twentieth as efficient in proteolysis of a test peptide substrate as the full length form, and Parks et al. (1995) indicate that the 27 kDa NIa proteinase appears to lose its activity with time.

Further, Polayes et al. (1994) disclose that the 27 kDa NIa proteinase is a highly specific protease that is active under a broad temperature range and on a variety of substrates. Polayes et al. report rapid cleavage at 30° C. and 37° C., about 80% cleavage at both 21° C. and 16° C. in one hour, and 50% cleavage at 4° C. Accordingly, Polayes et al. recommend the use of this proteinase as a tool for removing affinity tags from fusion proteins.

Use of 27 kDa NIa Proteinase Cleavage System for Purification of Proteins

Parks et al. (1994) disclose an improved method for the production, cleavage, and purification of fusion proteins and peptides using the 27 kDa NIa proteinase. The method comprises producing a fusion protein comprising the protein of interest, a carrier peptide (such as an affinity carrier) and a 27 kDa NIa proteinase cleavage site inserted between the two, purifying the fusion protein, and incubating the fusion protein with the 27 kDa Nia proteinase to remove the carrier peptide from the protein of interest.

Johnston et al., U.S. Pat. No. 5,532,142, disclose a similar method of isolation and purification of recombinant proteins using the 27 kDa NIa proteinase. Like the purification method of Parks et al. (1994), the method of Johnston et al. involves producing large quantities of the fusion protein containing a desired protein fused to the 27 kDa NIa proteinase cleavage site which is the carrier peptide, purifying the fusion protein, and incubating the purified fusion protein with the 27 kDa NIa proteinase to remove the carrier peptide from the desired protein.

Unlike other proteinases, the 27 kDa proteinase exhibits high specificity, insensitivity to many proteinase inhibitors used in protein purification, and efficient cleavage under a broad range of temperatures (Polayes et al., 1994). Moreover, the protein of interest is easily separated from the carrier peptide and the 27 kDa proteinase. For these reasons, there is an on-going interest in obtaining large quantities of the active protein for use as a tool in protein purification.

Purification of Proteins Including the 27 kDa NIa Proteinase from Inclusion Bodies Purification of Proteins that Form Inclusion Bodies. The development of recombinant DNA technology has enabled the cloning and expression of proteins in bacteria, yeast and mammalian cells and has made it possible to produce therapeutics and industrially important proteins at economically feasible levels. However, the expression of high levels of recombinant proteins in *Escherichia coli* often results in the formation of inactive, denatured protein that accumulates in intracellular aggregates known as insoluble inclusion bodies (Krueger et al., "Inclusion bodies from proteins produced at high levels in *Escherichia coli*," in Protein Folding, L. M. Gierasch and P. King (Eds), Am. Ass. Adv. Sci., 136-142 (1990); Marston, Biochem. J. 240:1-12 (1986); Mitraki et al., Bio/Technol. 7: 800-807 (1989); Schein, Bio/Technol. 7:1141-1147 (1989); Taylor et al., Bio/Technol. 4: 553-557 (1986)). Inclusion bodies are dense aggregates, which are 2-3 m in diameter and largely composed of recombinant protein, that can be separated from soluble bacterial proteins by low-speed centrifugation after cell lysis (Schoner et al., Biotechnology 3:151-154 (1985)).

The recovery of recombinantly expressed protein in the form of inclusion bodies has presented a number of problems. First, although the inclusion bodies contain a large percentage of the recombinantly produced protein, additional contaminating proteins must be removed in order to isolate the protein of interest. Second, the proteins localized in inclusion bodies are in a form that is not biologically active, presumably due to incorrect folding.

Several methods have been developed to obtain active proteins from inclusion bodies. These strategies include the separation and purification of inclusion bodies from other cellular components, solubilization and reduction of the insoluble material, purification of solubilized proteins and ultimately renaturation of the proteins and generation of native disulfide bonds. The art teaches that concentrations of 6 M or greater of chaotropic agents, such as guanidine hydrochloride, guanidine isothiocyanate or urea-are necessary for solubilization of the insoluble recombinant polypeptides from the inclusion bodies. See, for example, Vandenbroeck et al, Eur. J. Biochem. 215:481-486 (1993); Meagher et al., Biotech. Bioeng. 43:969-977 (1994); Yang et al., U.S. Pat. No. 4,705,848, issued Nov. 10, 1987; Weir et al., Biochem. J. 245:85-91 (1987); and Fischer, Biotech. Adv. 12:89-101 (1994). However, the use of high concentration of chaotropic agents, such as guanidine hydrochloride, to solubilize proteins denatures the proteins.

U.S. Pat. No. 5,912,327 discloses the use of low concentrations of guanidine salts, about 0.7 to about 3.5 M, to solubilize biologically active (i.e., correctly folded) proteins and extract this population of the protein from a heterogenous protein mixture localized in inclusion bodies. The method described in the patent comprises releasing the inclusion bodies containing the target protein from the cells by lysis, optionally washing the cells to remove cellular components, extracting with solutions containing low concentrations of guanidine salts, refolding target proteins which have been solubilized using guanidine salts by rapid dilution of guanidine salt extracts and optionally employing agents which facilitate target protein refolding. The protein can then be recovered and purified by methods well known to the skilled artisan. However, this method is labor intensive.

Tissue plasminogen activator (tPA or TPA) is one example of a pharmaceutically important drug produced by recombinant methods. Unfortunately the current methods for producing tPA from bacterial cell culture are both costly and laborious. The production of tPA in heterologous host organisms relies on the production of inactive tPA intracellularly in inclusion bodies, and the subsequent isolation and purification of such inclusion bodies, followed by activation of the tPA once freed from the inclusion bodies. U.S. Pat. No. 5,077,392 discloses a renaturation method for refolding denatured proteins obtained after expression in inclusion bodies. tPA is isolated as a denatured reduced protein and on subsequent oxidation refolded under oxidizing conditions to obtain what was reported as up to a 26% yield of "reactivated" protein. While the method appeared to improve polypeptide yield, the process involves multiple, time-consuming steps, due to the initial recovery of the insoluble, inactive protein.

Purification of 27 kDa NIa Proteinase. The 27 kDa NIA proteinase has been especially difficult to isolate and purify in large quantities and in active form because of its proclivity to form inclusion bodies in nature. Previously published purification protocols of TEV nuclear inclusion bodies from infected plant tissue have demonstrated considerable proteolytic activity (Dougherty et al., 1980). However, attempts to separate the 49 kDa NIa proteinase from the Nib protein and other components and to purify the NIa proteinase have resulted in loss of protein activity (Parks et al., 1995).

Parks et al. (1995) describe purification of the soluble fraction of recombinantly produced 27 kDa NIa proteinase. The purification method of Parks et al. involves overexpressing the recombinant form of the proteinase as a fusion protein comprising a seven-His tag at the N-terminus and purifying the fusion protein using two separate columns, a nickel-nitrilotriacetic acid-agarose (Ni-agarose) column and a cation-exchange column. This method is labor-intensive and produces insufficient quantities of proteinase for use as a general tool in protein purification.

Johnston et al., U.S. Pat. No. 5,532,142, discloses recombinant vectors for overproducing plant virus proteinases in suitable hosts. Johnston et al. use the same purification protocol as that of Parks et al. (1995) to purify the 27 kDa NIa proteinase. The yield of purified proteinase is typically in the range of 5 mg/liter of cell culture and not all of it is active. Thus, the yield of active protein is very low.

As discussed above, the 27 kDa NIA proteinase contains an internal self-cleavage site that when cleaved, produces a proteinase with reduced substrate cleavage activity. At the present, there is no known method of stabilizing the proteinase, and there is no known method of obtaining large quantities of purified active 27 kDa NIa proteinase in large quantities. Accordingly, there is a need to develop a method of obtaining large quantities of purified active 27 kDa proteinase that will not cleave itself.

SUMMARY OF THE INVENTION

The present invention provides mutant proteinases having a molecular weight of about 27 kDa and reduced self-cleavage activity relative to the self-cleavage activity of its wild-type proteinase. In one embodiment, the mutant proteinases of the present invention comprise an amino acid sequence in which the residue corresponding to Ser 219 of the wild-type 27 kDa NIa proteinase is replaced with another residue. In another embodiment, the mutant proteinases of the present invention comprises an amino acid sequence in which the residue corresponding to Ser 219 is replaced with Asn.

The present invention also provides composition comprising the mutant proteinase. Preferably, the composition comprises a carrier in addition to the mutant.

Moreover, the present invention provides fusion proteins comprising mutant proteinase having a molecular weight of about 27 kDa and reduced self-cleavage activity, fused to a heterologous polypeptide, fusion partner, or carrier protein. In one embodiment, the heterologous polypeptide, fusion partner, or carrier protein comprises a protein that facilitates its isolation. In a preferred embodiment, the heterologous polypeptide consists of six histidines.

The present invention includes nucleic acid molecules comprising a sequence encoding a mutant proteinase having a molecular weight of about 27 kDa and reduced self-cleavage activity relative to the self cleavage activity of to its wild-type proteinase. In one embodiment, the nucleic acid molecules encode mutant proteinases comprising an amino acid sequence in which the residue corresponding to Ser 219 of the 27 kDa NIa proteinase is replaced with another amino acid. In a preferred embodiment, the nucleic acid molecules encodes mutant proteinases comprising an amino acid sequence in which the residue corresponding to Ser 219 is replaced with Asn.

The present invention also includes vectors, expression vectors, and host cells comprising a nucleic acid molecule encoding a mutant proteinase having a molecular weight of about 27 kDa and reduced self-cleavage activity relative to the self-cleavage activity of its wild-type proteinase.

Further, the present invention includes nucleic acid molecules encoding fusion proteins comprising a proteinase, having a molecular weight of about 27 kDA and reduced self-cleavage activity relative to the self cleavage activity of its wild-type proteinase, fused to a heterologous protein.

The present invention provides methods of producing a proteinase having a molecular weight of about 27 kDa and reduced self-cleavage relative to the self-cleavage activity of its wild-type proteinase comprising cultivating a host cell comprising a nucleic acid encoding the proteinase under conditions that allow expression of the proteinase.

The present invention also provides a method of purifying a polypeptide that forms inclusion bodies in a cell comprising:
 a) obtaining cells expressing the polypeptide;
 b) lysing the cells;
 c) pelleting inclusion bodies by centrifugation of the lysed cells;
 d) centrifuging the inclusion bodies;
 e) solubilizing the inclusion bodies in buffer containing solubilization agent;
 f) centrifuging the solubilized inclusion bodies to obtain a supernatant containing the polypeptide;
 g) loading the supernatant over a single denaturing column;
 h) collecting the proteinase; and
 i) renaturing the collected polypeptide.

In one embodiment, the polypeptide to be purified is a proteinase having a molecular weight of about 27 kDa and reduced self-cleavage activity relative to the self-cleavage activity of its wild-type proteinase. In another embodiment, the polypeptide is selected from the group consisting of tobacco etch virus (TEV) 27kDa NIa proteinase and mutant 27 kDa NIa proteinase. In a preferred embodiment, the polypeptide is the mutant TPSN 27 kDa NIa proteinase, wherein the residue corresponding to Ser 219 of the wild-type 27 kDa NIa proteinase is replaced with Asn.

Contemplated denaturing column of step (g) includes column containing Ni-NTA resin. Contemplated methods of lysing the cells include freeze-thaw cycles, sonication, and other enzymatic and mechanical means. The present method also contemplates the addition of proteinase inhibitors, preferably but not limited to PMSF, leupeptin, and pepstatin A, to the cells before lysis. The present invention includes the use of buffers, solubilizing agent, renaturing agents well-known to the skilled artisan for purifying proteins.

Additionally, contemplated methods of using the proteinase having a molecular weight of 27 kDa and reduced self-cleavage activity, include cleavage of substrate. In one embodiment of using the proteinase, the proteinase is incubated with a protein for a sufficient amount of time to allow cleavage of the protein.

DETAILED DESCRIPTION OF THE INVENTION

A. General Description

Figure 1:
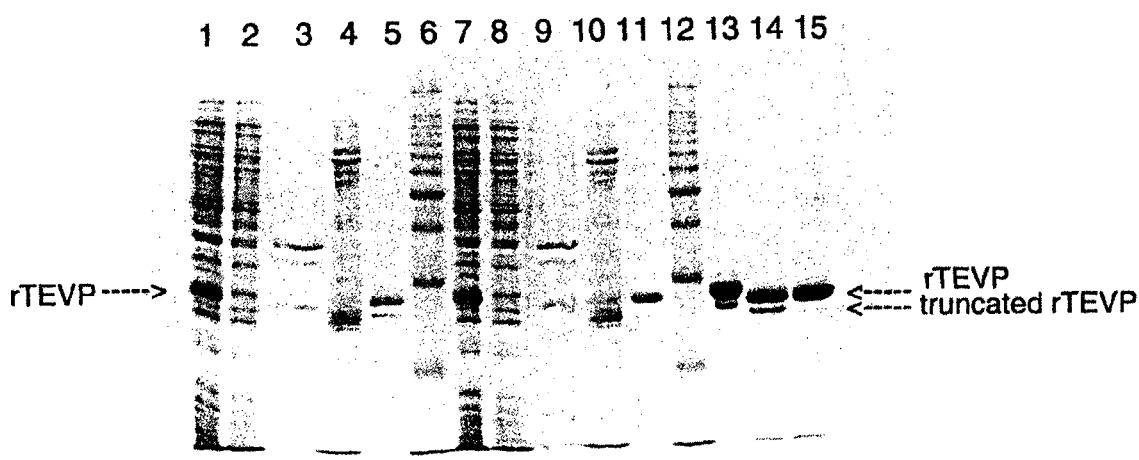
FIG. 1 shows 27 kDa NIa proteinase purification—soluble vs insoluble preps. Samples from the soluble and insoluble purifications of TPWT (wild-type 27 kDa NIa proteinase) and TPSN (mutant form with Ser→Asn mutation) show that most of the 27 kDa NIa proteinase was expressed in the insoluble fraction. Comparison of the final products from the different purifications shows that insoluble preparations produce greater yields with higher purity than soluble preparations. Overloaded, renatured TPWT and TPSN samples demonstrate sample purity as compared to a commercially available 27 kDa NIa proteinase.

The present invention is based on the unexpected discovery that a single amino acid change in the internal self-cleavage site will inhibit self-cleavage activity of the 27 kDa NIa proteinase. Mutating Ser at position 219 of the wild-type 27 kDa NIa proteinase to Asn prevents the proteinase from cleaving itself.

The present invention relates to expression, overproduction, and purification of virus proteinase. Sources of virus proteinase include flavi-, picoma- and potyviruses. The present method is considered particularly suited for overproducing potyvirus proteinases in *E. coli* or yeast cells.

The present invention is based on the development of a single-column purification method for isolation of milligram quantities of >95% pure, active 27 kDa NIa proteinase from inclusion body preparation. The newly developed purification method yields about 32 mg of total pure protein from the inclusion body preparation and greater than about 12 mg is active.

Accordingly, the present invention provides a method of obtaining large quantities of active 27 kDa NIa proteinase from inclusion body preparation. The present invention also provides a mutant 27 kDa NIa proteinase having the same substrate cleavage as the wild-type 27 kDa NIa proteinase and a reduced self-cleavage activity. Thus, the present invention provides a 27 kDa NIa proteinase with increased shelf-life.

B. Definitions

Unless defined otherwise, all technical and scientific terms used in this specification shall have the same meaning as commonly understood by persons of ordinary skill in the art to which the present invention pertains.

As used herein, "carrier" in a composition refers to a diluent, adjuvant, excipient, or vehicle with which the product is mixed.

As used herein, "carrier peptide or protein", "fusion partner", or "heterologous protein or polypeptide" of a fusion protein refers to the portion of the fusion protein that is added to the protein of interest for the purpose of purification, for stability in production, or for other reasons.

As used herein, "control sequence or element" or "regulatory sequence or element" refers to those non-translated regions of the vector, such as enhancers, promoters, 5' and 3' untranslated region, which interact with host cellular proteins to carry out transcription and translation.

As used herein, "homologs" refers to proteins having the same or similar functions, especially proteins from different species having the same or similar functions.

As used herein, "inclusion body" refers to distinctive structures frequently formed in the nucleus or cytoplasm in cells infected with certain filtrable viruses. They may be demonstrated by means of various stains.

As used herein, "internal self-cleavage activity" or "internal autocatalytic activity" of a protein refers to the activity of cleaving at some site within the protein itself.

As used herein, "internal self-cleavage site" or "internal autocatalytic site" is the site where the protein cleaves itself.

As used herein, "isolated nucleic acid" refers to a nucleic acid that has been separated from its naturally occurring environment.

As used herein, "isolated polypeptide or protein" refers to a polypeptide or protein that has been separated from its naturally occurring environment.

As used herein, "proteinase" and "protease" are interchangeable terms and refer to enzymes that hydrolyze (break) polypeptide chains.

As used herein, "mutant proteinase" is a proteinase obtained by altering the nucleic acid encoding the wild-type proteinase and expressing the altered nucleic acid. A "mutant" is a phenotype in which a mutation is manifested. A "mutation" is a change in the chemistry of a nucleic acid that is perpetuated in subsequent divisions of the cell in which it occurs.

As used herein, "specific activity" is defined as picomoles of substrate cleaved per picomole of proteinase in one hour at 30° C.

As used herein, "substrate cleavage activity" refers to the activity of a proteinase in cleaving a specific amino acid sequence with a specific amount of activity.

As used herein, "wild-type proteinase" is a naturally occurring proteinase.

As used herein, "27 kDa NIa proteinase or protease" refers to a proteinase having a molecular weight of about 27 kDa and having the same substrate cleavage activity as the wild-type 27 kDa NIa proteinase obtained from tobacco etch virus.

C. Specific Embodiments

1. Nucleic Acids Encoding Proteinases

The present invention provides nucleic acid molecules encoding proteinases having the same substrate cleavage activity as the wild-type 27 kDa NIa proteinase, and preferably the nucleic acid molecules are in isolated form. In one embodiment, nucleic acid molecules provided by the present invention encode a proteinase having 27 kDa and reduced self-cleavage activity as compared to the self-cleavage activity of its wild-type proteinase. In another embodiment, nucleic acid molecules of the present invention encode a mutant form of the 27 kDa NIa proteinase comprising an amino acid substitution corresponding to position 219 of its wild-type proteinase, preferably Ser substituted with Asn, having the same substrate cleavage activity as the wild-type proteinase and having reduced self-cleavage activity relative to its wild-type proteinase.

The nucleic acid molecules of the invention include deoxyribonucleic acids (DNAs), both single- and double-stranded deoxyribonucleic acids. However, they can also be ribonucleic acids (RNAs), as well as hybrid RNA:DNA double-stranded molecules. Contemplated nucleic acid molecules also include genomic DNA, cDNA, mRNA, and antisense molecules. The nucleic acids molecules of the present invention also include native or synthetic, RNA, DNA, or cDNA, that encode a proteinase protein, or the complementary strand thereof, including but not limited to nucleic acid found in a proteinase expressing organism, such as the tobacco etch virus.

The nucleic acid sequence encoding the proteinase can be, for instance, substantially or fully synthetic. See, for example, Goeddel et al., Proc. Natl. Acad. Sci. USA, 76, 106-110, 1979. For recombinant expression purposes, codon usage preferences for the organism in which such a nucleic acid is to be expressed are advantageously considered in designing a synthetic proteinase-encoding nucleic acid. Codon usage preferences for different organisms are well known to the skilled artisan. Since the nucleic acid code is degenerate, numerous nucleic acid sequences can be used to create the same amino acid sequence.

The nucleic acid molecules of the present invention can encode proteinases having the same substrate cleavage activity as a wild-type 27 kDa NIa proteinase. For example, the nucleic acid molecules can encode a proteinase having 27 kDa and reduced self-cleavage activity or a mutant form of the 27 kDa NIa proteinase having the same substrate cleavage activity and having reduced self-cleavage activity as compared with its wild-type proteinase, piconaviral 3C proteinases, cellular serine proteinases such as chymotrypsin trypsin proteinases, proteinases that have internal self-cleavage sites similar to the internal self-cleavage site of the 27 kDa NIa proteinase, mutant forms of such proteinases with reduced self-cleavage activity as compared to its wild-type proteinase, and proteinases that recognize the same extended seven amino acid sequence (E-X-X-Y-X-Q↓S/G) (SEQ ID NO: 1) substrate cleavage site as the 27 kDa NIa proteinase.

In one embodiment, the nucleic acids of the present invention encode a proteinase having 27 kDa and reduced self-cleavage activity as compared to its wild-type proteinase. In another embodiment, the nucleic acids of the present invention encode a mutant form of the 27 kDa NIa proteinase comprising an amino acid sequence in which the residue corresponding to 219 of the 27 kDa NIa proteinase is replaced with another residue, preferably Asn.

Nucleic Acid Molecules Encoding Mutant Forms and Allelic Forms of Proteinases. To construct mutant forms of proteinases having the same substrate cleavage activity as the wild-type 27 kDa NIa proteinase and having reduced self-cleavage activity, the nucleic acid encoding the wild-type proteinase can be used as a starting point and modified to form the desired mutants. For example, in the preferred embodiment, the nucleic acid sequence encoding the wild-type 27 kDa NIa proteinase is mutated such that the Ser corresponding to position 219 in the encoded amino acid sequence is replaced with another amino acid, preferably Asn.

Further, with an altered amino acid sequence, numerous methods are known to delete sequence from or mutate nucleic acid sequences that encode a polypeptide and to confirm the function of the polypeptides encoded by these deleted or mutated sequences. Accordingly, the invention also relates to a mutated or deleted version of a proteinase nucleic acid that encodes a proteinase that has the same substrate cleavage activity as the wild-type 27 kDa NIa proteinase.

Conservative variants of the wild-type 27 kDa NIa proteinases or its naturally occurring isoforms and homologs are encompassed by the present invention. Such conservative mutations include mutations that switch one amino acid for another within one of the following groups:

1. Small aliphatic, nonpolar or slightly polar residues: Ala, Ser, Thr, Pro and Gly;
2. Polar, negatively charged residues and their amides: Asp, Asn, Glu and Gln;
3. Polar, positively charged residues: His, Arg and Lys;
4. Large aliphatic, nonpolar residues: Met, Leu, Ile, Val and Cys; and
5. Aromatic residues: Phe, Tyr and Trp.

The types of substitutions selected may be based on the analysis of the frequencies of amino acid substitutions between homologous proteins of different species developed by Schulz et al., Principles of Protein Structure, Springer-Verlag, 1978, pp. 14-16, on the analysis of structure-forming potentials developed by Chou and Fasman, Biochemistry 13, 211, 1974 or other such methods reviewed by Schulz et al., Principles in Protein Structure, Springer-Verlag, 1978, pp. 108-130, and on the analysis of hydrophobicity patterns in proteins developed by Kyte and Doolittle, J. Mol. Biol. 157: 105-132, 1982.

The present invention also contemplates nucleic acids encoding naturally occurring allelic variants of the proteinases described above. In a preferred embodiment, allelic variants even though possessing a slightly different amino acid sequence than the naturally occurring wild-type 27 kDa proteinase will have the requisite ability to recognize and cleave the heptapeptide sequence E-X-X-Y-X-Q↓S/G (SEQ ID NO: 1). The present invention also contemplates conservative variants that do not affect the ability of the proteinase to recognize and cleave the heptapeptide sequence E-X-X-Y-X-Q↓S/G (SEQ ID NO: 1). The present invention includes 27 kDa NIa proteinase with altered overall charge, structure, hydrophobic/hydrophilic properties by amino acid substitutions, insertions, or deletions but still possess the ability to recognize and cleave the heptapeptide.

Preferably, the nucleic acids will encode proteinases having the same substrate cleavage activity as the wild-type 27 kDa NIa proteinase and having at least about 70% sequence identity, more preferably, at least about 80% sequence identity, even more preferably, at least about 85% sequence identity, yet more preferably at least about 90% sequence identity, and most preferably at least about 95% sequence identity to a wild-type 27 kDa NIa proteinase or other naturally occurring isoforms having the same substrate cleavage activity.

Numerous methods for determining percent homology are known in the art. One preferred method is to use version 6.0 of the GAP computer program for making sequence comparisons. The program is available from the University of Wisconsin Genetics Computer Group and utilizes the alignment method of Needleman and Wunsch, J. Mol. Biol. 48, 443, 1970, as revised by Smith and Waterman Adv. Appl. Math. 2, 482, 1981. Numerous methods for determining percent identity are also known in the art, and a preferred method is to use the FASTA computer program, which is also available from the University of Wisconsin Genetics Computer Group.

Additionally, the invention includes substantially pure nucleic acids that hybridize under stringent conditions to a nucleic acid encoding a proteinase having the same substrate cleavage activity as the wild-type 27 kDa NIa proteinase. Stringent hybridization conditions are conditions in which hybridization to a labeled known nucleic acid sequence yields a clear and detectable sequence. Stringent conditions are those that (1) employ low ionic strength and high temperature for washing, for example, with 0.015 M NaCl, 0.0015 M sodium titrate, 0.1% SDS at 50° C.; (2) employ during hybridization a denaturing agent such as formamide, for example, 50% (vol/vol) formamide with 0.1% bovine serum albumin, 0.1% Ficoll, 0.1% polyvinylpyrrolidone, 50 mM sodium phosphate buffer at pH 6.5 with 750 mM NaCl, 75 mM sodium citrate at 42° C.; and (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., followed with washes at 42° C. in 0.2×SSC and 0.1% SDS. A skilled artisan can readily determine and vary the stringency conditions appropriately to obtain a clear and detectable hybridization signal.

Nucleic Acid Molecules Encoding Fusion Proteins. The nucleic acid molecules of the present invention also encode fusion proteins comprising a proteinase such as those described in the previous paragraphs fused to a heterologous protein or polypeptide. In one embodiment, the fusion proteins of the present invention comprise the proteinase having 27 kDa and reduced self-cleavage activity as compared to its wild-type proteinase fused to a heterologous protein. In another embodiment, the fusion protein comprises the mutant 27 kDa NIa proteinase comprising an amino acid sequence in which the residue corresponding to Ser 219 of the 27 kDa NIa proteinase is replaced with another residue, preferably Asn, fused to a heterologous protein.

Nucleic acids encoding various heterologous proteins may be fused to the nucleic acid encoding the proteinase. For example, nucleic acid encoding affinity tags such as the His tags, antibodies, or carrier peptides or proteins having specific binding properties such as *Staphylococcus aureus* protein A and the carbohydrate recognition domain (CRD) of galactose-specific rat hepatic lectin (Taylor and Drickamer, 1991), may be fused to the proteinase for purification of the proteinase by affinity chromatography. Nucleic acid encoding substrate cleavage sites of thrombin or factor X may be fused to the nucleic acid encoding the proteinase for ease of removal of carrier peptide. Additionally, fusion proteins tend to be more soluble than a single protein, contributing to higher yields and simpler purification. The fusion partner for the proteinase may be selected on the basis of transport characteristics to assure that the fusion protein is secreted into either the periplasmic space or the growth medium. Moreover, the fusion partner may also be selected for increasing the stability of the proteinase in the preferred expression system for obtaining large quantities of the protein. For example, fusion proteins are usually more stable in bacteria than the native eukaryotic proteinase.

Nucleic Acid Encoding Proteins or Polypeptides Expressed in Inclusion Bodies. Nucleic acids encoding proteins, polypeptides, or fusion proteins or polypeptides that form inclusion bodies in cells are also encompassed by the present application. Such nucleic acids can be expressed in host cells to produce large quantities of the proteins or polypeptides in inclusion bodies, as discussed below. The proteins or polypeptides are then purified by the purification method provided by the present invention, also discussed below.

2. Polypeptides or Proteins

Polypeptides of the invention include all proteinases having the same substrate cleavage activity as the wild-type 27 kDa NIa proteinase, and preferably in isolated or purified form. The present invention also includes these proteinases in native or synthetic form, including but not limited to polypeptides purified from a proteinase-expressing organism. In one embodiment, the polypeptides of the present invention comprise a proteinase having 27 kDa and reduced self-cleavage activity as compared to its wild-type proteinase. In another embodiment, the polypeptides of the present invention comprise a mutant form of the wild-type 27 kDa NIa proteinase having the same substrate cleavage activity as the wild-type proteinase, but with reduced self-cleavage activity as compared to its wild-type proteinase, and having amino acid corresponding to position 219 of the wild-type NIa proteinase substituted with another amino acid, preferably Asn.

Structurally, the 27 kDa NIa proteinase has been reported to be similar to the trypsin-like family of cellular serine proteinases, such as chymotrypsin or trypsin, with the substitution of Cys for serine as the active site nucleophile (Blazan et al., 1990; Dougherty et al., 1989). Dougherty et al. (1989) discloses the catalytic triad of 27 kDa NIa proteinase to be composed of His, Asp, and Cys which is similar to the catalytic triad found in other viral proteinases (Dougherty et al., 1989). However, unlike the other proteinases, the 27 kDa proteinase recognizes an extended heptapeptide sequence, E-X-X-Y-X-Q↓S/G (positions P6-P1↓P'1; X is any amino acid) (SEQ ID NO: 1), and cleaves within the heptapeptide sequence (Dougherty et al., 1989a; Dougherty et al., 1988; Dougherty et al., 1989b).

Proteinases having the same substrate cleavage activity as a wild-type 27 kDa NIa proteinase include but are not limited to polypeptides comprising the wild-type 27 kDa NIa proteinase or a mutant form thereof having the same substrate cleavage activity and having reduced self-cleavage activity as compared with its wild-type proteinase, piconaviral 3C proteinases, cellular serine proteinases such as chymotrypsin trypsin proteinases, proteinases that have internal self-cleavage sites similar to the internal self-cleavage site of the 27 kDa NIa proteinase, mutant forms of such proteinases with reduced self-cleavage activity as compared to its wild-type proteinase, and proteinases that recognize the same extended seven amino acid sequence (E-X-X-Y-X-Q↓S/G, SEQ ID NO: 1) substrate cleavage site as the 27 kDa NIa proteinase.

In one embodiment, polypeptides of the present invention comprise a proteinase having a molecular weight of 27 kDa and reduced self-cleavage activity as compared to the wild-type 27 kDa NIa proteinase. In another embodiment, the polypeptides of the present invention comprise the mutant form of the 27 kDa NIa proteinase having an amino acid sequence in which the residue corresponding to Ser219 of the 27 kDa NIa proteinase is replaced with another residue, preferably Asn.

Mutant Forms and Allelic Forms of Proteinases. The present invention also include mutant forms of proteinases having the same substrate cleavage activity as the wild-type 27 kDa NIa proteinase and having reduced self-cleavage activity. As discussed above, to construct mutant forms of proteinases, the nucleic acid encoding the wild-type proteinase can be used as a starting point and modified to form the desired mutants. For example, in the preferred embodiment, the nucleic acid sequence encoding the wild-type 27 kDa NIa proteinase is mutated such that Ser corresponding to position 219 in the encoded amino acid sequence is replaced with another amino acid, preferably Asn. Further, numerous methods are known to delete and mutate nucleic acid sequences that encode a polypeptide and to confirm the function of the polypeptides encoded by these deleted or mutated sequences. Accordingly, the invention also provides mutated or deleted version of a proteinase that has the same substrate cleavage activity as the wild-type 27 kDa NIa proteinase.

Conservative variants of the wild-type 27 kDa NIa proteinases or its naturally occurring isoforms and homologs are encompassed. Such conservative mutations have been discussed under the previous section. The present invention also contemplates conservative variants that do not affect the ability of the proteinase to recognize and cleave the heptapeptide sequence E-X-X-Y-X-Q↓S/G (SEQ ID NO: 1). The present invention includes 27 kDa NIa proteinase with altered overall charge, structure, hydrophobic/hydrophilic properties by amino acid substitutions, insertions, or deletions but still possess the ability to recognize and cleave the heptapeptide.

The present invention also contemplates naturally occurring allelic variants of the proteinases having the same substrate cleavage activity as the 27 kDa NIa proteinase. In a preferred embodiment, allelic variants even though possessing a slightly different amino acid sequence than the naturally occurring wild-type 27 kDa proteinase will have the requisite ability to recognize and cleave the heptapeptide sequence E-X-X-Y-X-Q↓SG (SEQ ID NO: 1).

Preferably, proteinases having the same substrate cleavage activity as the wild-type 27 kDa NIa proteinase and at least about 70% sequence identity, more preferably, at least about 80% sequence identity, even more preferably, at least about 85% sequence identity, yet more preferably at least about 90% sequence identity, and most preferably at least about 95% sequence identity to a wild-type 27 kDa NIa proteinase or other naturally occurring isoforms having the same substrate cleavage activity.

Numerous methods for determining percent homology are known in the art. One preferred method is to use version 6.0 of the GAP computer program for making sequence comparisons. The program is available from the University of Wisconsin Genetics Computer Group and utilizes the alignment method of Needleman and Wunsch, J. Mol. Biol. 48, 443, 1970, as revised by Smith and Waterman Adv. Appl. Math. 2, 482, 1981. Numerous methods for determining percent identity are also known in the art, and a preferred method is to use the FASTA computer program, which is also available from the University of Wisconsin Genetics Computer Group.

Fusion Proteins. The present invention also provides fusion proteins comprising a proteinase having the same substrate cleavage activity as the 27 kDa NIa proteinase fused to a heterologous protein or polypeptide. In one embodiment, the fusion proteins of the present invention comprise a proteinase having a molecular weight of about 27 kDa and reduced self-cleavage activity as compared to its wild-type proteinase fused to a heterologous protein. In another embodiment, the fusion proteins of the present invention comprise a mutant 27 kDa NIa proteinase having an amino acid sequence in which the residue corresponding to Ser219 of the 27 kDa NIa proteinase is replaced with another residue, preferably Asn, fused to a heterologous protein.

As discussed earlier, various heterologous proteins may be fused to the proteinase of the present invention (see below also).

Compositions. The present invention also provides compositions comprising an isolated proteinase having the same substrate cleavage activity as the wild-type 27 kDa NIa proteinase and a carrier. The composition may comprise a dry formulation or an aqueous solution. The carrier may be any compound that does not affect the substrate cleavage activity of the proteinase. Carrier could be a diluent, an excipient, or even a stabilizer. A specific example of a carrier could be buffer or water, which does not affect the stability of the proteinase.

Uses of Proteinases with Identical Substrate Cleavage Activity as the 27 kDa NIa Proteinase. The present invention also provides methods of using proteinases with the same substrate cleavage activity as the 27 kDa NIa proteinase. Proteinases of the present invention can be used to cleave polypeptides comprising the heptapeptide sequence E-X-X-Y-X-Q↓S/G (SEQ ID NO: 1). The mutant forms of the 27 kDa NIa proteinase with decreased self cleavage activity are more stable than the wild-type proteinase and have a longer shelf-life.

As discussed earlier, Parks et al. (1994) and Johnson et al., U.S. Pat. No. 5,532,142, disclose the use of the 27 kDa NIa proteinase as a tool for purifying and obtaining large quantities of desired proteins. As shown by Parks et al. and Johnson et al., to obtain large quantities of a desired protein, the protein is fused to a carrier protein and a substrate cleavage site recognized by the 27 kDa NIa proteinase is inserted between the two proteins. The 27 kDa NIa proteinase is selected for separating the carrier protein from the desired protein because the 27 kDa NIa proteinase exhibits unique characteristics. Unlike other proteinases, the 27 kDa proteinase exhibits high specificity, insensitivity to many proteinase inhibitors used in protein purification, and efficient cleavage under broad range of temperatures (Polayes et al., 1994). Moreover, the protein of interest can be easily separated from the carrier peptide and the 27 kDa proteinase.

The present invention provides mutant forms of the 27 kDa NIa proteinase with the same substrate activity as the wild-type proteinase and with decreased self-cleavage activity. The mutant 27 kDa NIa proteinases of the present invention are also useful as tools for purifying and obtaining large quantities of desired proteins.

Proteins or Polypeptides that Form Inclusion Bodies. Proteins, polypeptides, fusion proteins or polypeptides that form inclusion bodies in cells are also encompassed by the present application. Such proteins, polypeptides, or fusion proteins, either produced by recombinant means or present in their native source, are then purified by the purification method provided by the present invention, discussed below.

In a preferred embodiment, the fusion proteins comprising a protein of interest is fused to a carrier protein or fusion partner that facilitates its isolation. Examples of carrier proteins are not limited to any particular protein, but may be selected from a wide variety of proteins such as beta galactosidase, ubiquitin, glutathione S-transferase, alkaline phosphatase, maltose binding protein, Protein A, polyhistidines, monoclonal antibody epitopes and so forth. Carrier proteins typically will be selected on the basis of characteristics contributing to easy isolation, most desirable being those that are readily secreted by the microorganisms or which have some property or feature which facilitates isolation and purification of the protein. Glutathione S-transferase, maltose binding protein and polyhistidine sequences, for example, are generally preferred because there are readily available affinity columns to which they can be bound and eluted. Other suitable fusion partners include antigenic tags that readily bind to corresponding antibodies or proteins that have special affinity properties, for example, selective binding to particular metals, as with polyhistidine peptide binding to nickel.

3. Recombinant Production of Proteinases

Vectors and Expression vectors. The present invention provides vectors and expression vectors comprising a nucleic acid encoding a proteinase having the same substrate cleavage activity as the wild-type 27 kDa NIa proteinase. In a preferred embodiment, the vectors or expression vectors comprise a nucleic acid encoding a proteinase having a molecular weight of about 27 kDa and reduced self-cleavage activity as compared to its wild-type proteinase. In a more preferred embodiment, the vectors or expression vectors comprise the nucleic acid encoding a mutant form of the 27 kDa NIa proteinase having the same substrate cleavage activity as its wild-type 27 kDa NIa proteinase and reduced self-cleavage activity as compared to its wild-type proteinase.

The present invention also provides vectors and expression vectors containing the nucleic acids encoding fusion proteins and encoding any protein that forms inclusion bodies in cells. Preferably, the fusion proteins comprise a proteinase having the same substrate cleavage activity as the 27kDa NIa proteinase and a heterologous protein. More preferably, the proteinase of the fusion protein is a mutant form of 27 kDa NIa proteinase having reduced self-cleavage activity and has an amino acid sequence in which the residue corresponding to position 240 is replaced with another amino acid, preferably Asn.

Vectors or cassettes useful for the transformation and transfection of suitable host cells are well known in the art. Typically, the vectors or cassettes contain sequences directing transcription and/or translation of the relevant gene, a selectable marker, and sequences allowing autonomous replication or chromosomal integration. In an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

Suitable vectors for the present invention comprise a region 5' of the gene which harbors transcriptional initiation regulation or control and a region 3' of the DNA fragment which regulates transcriptional termination. It is most preferred when both regulatory regions are derived from nucleic acids homologous to the transformed host cell, although it is to be understood that such regulatory regions need not be derived from the nucleic acids native to the specific species chosen as a production host.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, Calif.) or PSPORT1 plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding the proteinase or protein formed in inclusion bodies, vectors based on SV40 or EBV may be used with an appropriate selectable marker.

In bacterial systems, a number of expression vectors may be selected depending upon the use intended for the proteinase or protein that forms inclusion bodies in a cell. For example, when large quantities of the protein are needed for the induction of antibodies or for use as a tool in the purification of proteins, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding the proteinase may be ligated into the vector in frame with sequences for the amino-terminal Met and the subsequent 7 residues of β-galactosidase so that a hybrid protein is produced. An example of such a vector include pIN vectors (Van Heeke, G. and S. M. Schuster (1989) J. Biol. Chem. 264:5503-5509).

pGEX vectors (Promega, Madison, Wis.) are used to express foreign polypeptides as fusion proteins with a heterologous protein such as glutathione S-transferase (GST). In general, fusion proteins are soluble and can easily be purified from lysed cells by adsorption to glutathione-agarose beads followed by elution in the presence of free glutathione. Proteins made in such systems may be designed to include a protease cleavage site, such as the substrate cleavage site of the 27 kDa NIa proteinase, so that the purified polypeptide of interest can be easily released from the GST moiety. The fusion proteins may also comprise a preferred proteinase or any protein that forms inclusion bodies in a cell and a carrier peptide or protein, such as the His tag, for affinity purification of the proteinase or protein. A further discussion of vectors which contain fusion proteins is provided in Kroll, D. J. et al. (1993; DNA Cell Biol. 12:441-453).

In the yeast, *Saccharomyces cerevisiae*, a number of vectors containing constitutive or inducible promoters such as alpha factor, alcohol oxidase, and PGH may be used (Grant et al. (1987) Methods Enzymol. 153:516-544). In cases where plant expression vectors are used, the expression of sequences encoding the proteinase or protein that forms inclusion bodies in a cell may be driven by any of a number of promoters. For example, viral promoters such as the 35S and 19S promoters of CAMV may be used alone or in combination with the omega leader sequence from TMV (Takamatsu, N. (1987) EMBO J. 6:307-311). Alternatively, plant promoters such as the small subunit of RUBISCO or heat shock promoters may be used (Coruzzi, G. et al. (1984) EMBO J. 3:1671-1680; Broglie, R. et al. (1984) Science 224:838-843; and Winter, J. et al. (1991) Results Probi. Cell Dfffer. 17:85-105). These constructs can be introduced into plant cells by direct DNA transformation or pathogen-mediated transfection. Such techniques are described in a number of generally available reviews (see, for example, Murry, L. E. in McGraw Hill Yearbook of Science and Technology (1992) McGraw Hill, New York, N.Y.; pp. 191-196).

An insect system may also be used to express the proteinase or protein that forms inclusion bodies in a cell. For example, in one such system, *Autographa californica* nuclear polyhedrosis virus (AcNPV) is used as a vector to express foreign genes in *Spodoptera frugiperda* cells or in *Trichoplusia larvae*. The sequences encoding the protein may be cloned into a non-essential region of the virus, such as the polyhedrin gene, and placed under control of the polyhedrin promoter. Successful insertion of the protein will render the polyhedrin gene inactive and produce recombinant virus lacking coat protein. The recombinant viruses may then be used to infect, for example, *S. frugiperda* cells or *Trichoplusia larvae* in which PLBP may be expressed (Engelhard, E. K. el. al. (1994) Proc. Nat. Acad. Sci. 91:3224-3227).

In mammalian host cells, a number of viral-based expression systems may be utilized. In cases where an adenovirus is used as an expression vector, sequences encoding the proteinase or protein that form inclusion bodies in a cell may be ligated into an adenovirus transcription/translation complex consisting of the late promoter and tripartite leader sequence. Insertion in a non-essential E1 or E3 region of the viral genome may be used to obtain a viable virus which is capable of expressing PLBP in infected host cells (Logan, J. and Shenk, T. (1984) Proc. Natl. Acad. Sci. 81:3655-3659). In addition, transcription enhancers, such as the Rous sarcoma virus (RSV) enhancer, may be used to increase expression in mammalian host cells.

Specific initiation signals may also be used to achieve more efficient translation of sequences encoding the proteinase or protein formed in inclusion bodies. Such signals include the ATG initiation codon and adjacent sequences. In cases where sequences encoding a protein, its initiation codon, and upstream sequences are inserted into the appropriate expression vector, no additional transcriptional or translational regulatory signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125-162).

Host Cells. The present invention also provides host cells, comprising a nucleic acid sequence encoding a proteinase as described above or a protein that forms inclusion bodies in a cell, which are used in the recombinant production of the encoding the proteinase or protein. A vector comprising the nucleic acid sequence of the present invention is introduced into a host cell so that the vector is maintained as a chromosomal integrant or as a self-replicating extra-chromosomal vector as described earlier. The choice of a host cell will to a large extent depend upon the gene encoding the polypeptide and its source. The host cell may be a unicellular microorganism, e.g., a prokaryote, or a non-unicellular microorganism, e.g., a eukaryote. The host cell may be a eukaryote selected from the group consisting of mammalian cell, insect cell, plant cell or fungal cell.

Useful unicellular cells are bacterial cells such as gram positive bacteria including, but not limited to, a *Bacillus* cell, e.g., *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis,* and *Bacillus thuringiensis*; or a *Streptomyces* cell, e.g., *Streptomyces lividans* or *Streptomyces murinus*, or gram negative bacteria such as *E. coli* and *Pseudomonas* sp. In a preferred embodiment, the bacterial host cell is *E. Coli*. Various strains of *E. coli* (e.g., HB101, DH5, DH10, and MC1061) are well-known as host cells in the field of biotechnology.

Mammalian cells, such as Chinese hamster ovary cells (CHO) or 3T3 cells may be used in the present invention. The selection of suitable mammalian host cells and methods for transformation, culture, amplification, screening and product production and purification are known in the art. Other suitable mammalian cell lines, are the monkey COS-1 and COS-7 cell lines, and the CV-1 cell line. Further exemplary mammalian host cells include primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or may contain a dominantly acting selection gene. Other suitable mammalian cell lines include but are not limited to, HeLa, mouse L-929 cells, 3T3 lines derived from Swiss, Balb-c or NIH mice, BHK or HaK hamster cell lines.

Many strains of yeast cells known to those skilled in the art are also available as host cells for expression of the polypeptides of the present invention. Additionally, where desired, insect cells may be utilized as host cells in the method of the present invention (Miller et al., 1986 Genetic Engineering 8:277-298).

The introduction of a vector into a bacterial host cell may, for instance, be effected by protoplast transformation (see, e.g., Chang and Cohen, 1979, Molecular General Genetics 168: 111-115), using competent cells (see, e.g., Young and Spizizin, 1961, Journal of Bacteriology 81: 823-829, or Dubnau and Davidoff-Abelson, 1971, Journal of Molecular Biology 56: 209-221), electroporation (see, e.g., Shigekawa and Dower, 1988, Biotechniques 6: 742-751), or conjugation (see, e.g., Koehler and Thorne, 1987, Journal of Bacteriology 169: 5771-5278).

Host cells transformed with nucleotide sequences encoding proteinase and protein that form inclusion bodies may be cultured under conditions suitable for the expression and recovery of the proteinase from cell culture. The protein produced by a transformed cell may be secreted, contained intracellularly, or contained with the inclusion factor depending on the sequence and/or the vector used. As will be understood by those of skill in the art, expression vectors containing polynucleotides which encode the protein may be designed to contain signal sequences which direct secretion of the protein through a prokaryotic or eukaryotic cell membrane.

Other constructions may be used to join sequences encoding the protein to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) or the 27 kDa NIa proteinase cleavage site between the purification domain and the protein may be used to facilitate purification. One such expression vector provides for expression of a fusion protein containing the protein and a nucleic acid encoding 6 histidine residues preceding a thioredoxin or an enterokinase cleavage site. The histidine residues facilitate purification on IMAC (immobilized metal ion affinity chromatography) as described in Porath, J. et al. (1992, Prot. Exp. Purif. 3: 263-281) while the enterokinase cleavage site provides a means for purifying from the fusion protein.

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells which have specific cellular machinery and characteristic mechanisms for post-translational activities (e.g., CHO, HeLa, MDCK, HEK293, and WI38), are available from the American Type Culture Collection (ATCC; 10801 University Boulevard, Manassas, Va., 20110-2209) and may be chosen to ensure the correct modification and processing of the foreign protein.

For long-term, high-yield production of proteinases or proteins that form inclusion bodies in a cell, stable expression is preferred. For example, cell lines which stably express proteinase or proteins that form inclusion bodies may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223-32) and adenine phosphoribosyltransferase (Lowy, I. et al. (1980) Cell 22:817-23) genes which can be employed in tk⁻ or aprt⁻ cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567-70); npt, which confers resistance to the aminoglycosides, neomycin and G-418 (Colbere-Garapin, F. et al. (1981) J. Mol. Biol. 150:1-14); and als or pat, which confers resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047-51). Recently, the use of visible markers has gained popularity with such markers as anthocyanins, -glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121-131).

Although the presence/absence of marker gene expression suggests that the gene of interest is also present, its presence and expression may need to be confirmed. For example, if the sequence encoding a proteinase or a protein that forms inclusion bodies in a cell, is inserted within a marker gene sequence, transformed cells containing sequences encoding the protein can be identified by the absence of marker gene function. Alternatively, a marker gene can be placed in tandem with a sequence encoding protein under the control of a single promoter. Expression of the marker gene in response to induction or selection usually indicates expression of the tandem gene as well. Alternatively, host cells which contain the nucleic acid sequence encoding the protein and express the protein may be identified by a variety of procedures known to those of skill in the art. These procedures include, but are not limited to, DNA-DNA or DNA-RNA hybridizations and substrate cleavage assay or immunoassay techniques which include membrane, solution, or chip based technologies for the detection and/or quantification of nucleic acid or protein.

Production of Protein from Host Cells. The present invention also provides methods for producing a proteinase or a protein that forms inclusion body in a cell comprising (a) cultivating the host cell under conditions that allow expression of the protein; and (b) recovering the protein. The proteinase of the present invention has a substrate cleavage activity that is identical to that of the 27 kDa NIa proteinase. Preferably, the proteinase has a molecular weight of about 27 kDa and a reduced self-cleavage activity as compared to its wild-type proteinase. More preferably, the proteinase is a mutant form of the 27 kDa NIa proteinase, and comprises an amino acid sequence in which the residue corresponding to position 219 of the wild-type 27 kDa NIa is replaced with another amino acid, preferably Asn.

In the production methods of the present invention, the cells are cultivated in a nutrient medium suitable for production of the proteins of the present invention using methods known in the art. For example, the cell may be cultivated by shake-flask cultivation, small-scale or large-scale fermentation (including continuous, batch, fed-batch, or solid state fermentations) in laboratory or industrial fermenters performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the protein is secreted into the nutrient medium, the polypeptide can be recovered directly from the medium. If the protein is not secreted, it can be recovered from cell lysates as described below The proteins may be detected using methods known in the art that are specific for the polypeptides. These detection methods may include use of specific antibodies, formation of an enzyme product, or disappearance of an enzyme substrate. For example, an enzyme assay may be used to determine the activity of the protein.

The resulting protein may be recovered by methods described below.

4. Purification of Proteins

General Procedure for Purification of Proteins. The proteins of the present invention produced from host cells may be recovered by methods known in the art. For example, the polypeptide may be recovered from the nutrient medium by conventional procedures including, but not limited to, centrifugation, filtration, extraction, spray-drying, evaporation, or precipitation.

The proteins of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g. ammonium sulfate precipitation), SDS-PAGE, or extraction (see, e.g., Protein Purification, J.-C. Janson and Lars Ryden, editors, VCH Publishers, New York, 1989).

In one embodiment of the invention, when the protein is secreted into the culture medium, the step of collecting the conditioned culture medium is followed by the step of purifying the protein. The protein in the collected medium may be purified by any method known in the art, such as selective precipitation, affinity chromatography, dialysis, immunoprecipitation, ion-exchange chromatography, size-exclusion chromatography, hydrophobic interaction chromatography, or reversed-phase chromatography (Guide to Protein Purification, in Methods in Enzymology 182 Murray P. Deutscher ed., 1990), Remington: The Science and Practice of Pharmacy 534-58 (Alfonso R. Gennaro ed., 19th ed. 1995)). Chromatography can be carried out using conventional columns or by HPLC (high performance liquid chromatography) or FPLC (fast protein liquid chromatography).

In another embodiment of the invention, the protein is purified by anion-exchange chromatography. Methods of purifying proteins using anion-exchange chromatography are well known to those skilled in the art (See, e.g., Edward R. Rossomando, Ion-Exchange Chromatography, in Guide to Protein Purification, Methods of Enzymology 182, 309-16 (Murray P. Deutscher ed., 1990)). In an alternate embodiment of the invention, the protein is purified by affinity chromatography over a protamine-agarose column, such as a protamine-Sepharose® (Pharmacia-LKB) column. Methods of purifying the proteins of the present invention using protamine-agarose columns are known to those skilled in the art (Dempfle and Heene, Thromb. Res. 46, 19 (1987)). Preferably, the proteins of the present invention are purified by affinity chromatography using a column containing Ni-NTA Superflow resin (nickel-nitilotriacetic acid-agarose, Qiagen)

In an alternate embodiment of the invention, the protein is purified by immunoaffinity chromatography using polyclonal or monoclonal antibodies raised against the intact protein or peptides thereof of the present invention. Methods of producing and using polyclonal and monoclonal antibodies are well known in the art (Ed Harlow & David Lane, Antibodies: A Laboratory Manual (1988); Norman A. Staines, Monoclonal Antibodies, in Biochemical Research Techniques: A Practical Introduction (John M. Wrigglesworth Ed., 1983)). Likewise, methods of performing affinity chromatography using polyclonal and monoclonal antibodies are also well known in the art. (Ed Harlow & David Lane, Antibodies: A Laboratory Manual (1988); Steven Ostrove, Affinity Chromatography.

General Methods, in Guide to Protein Purification, Methods of Enzymology 182, 357-71 (Murray P. Deutscher ed., 1990)).

In another embodiment of the invention, when the protein is not secreted into the culture medium, it is necessary to remove the protein from the cell by lysing the cells using methods well known in the art such as sonication or freeze-thawing, followed by isolating the protein from the cell extract. The cell extract may be prepared or incubated in the presence of cell protease inhibitors. The plant virus cleavage site is not susceptible to proteolysis by ordinary cell proteases. The plant virus proteinase itself is unaffected by ordinary protease inhibitors so that such inhibitors may be added in amounts sufficient to inactivate cell proteases. Typical and commonly used cell protease inhibitors include leupeptin, pepstatin A, PMSF, E-64, TLCK, bestatin and aprotinin. However, any of a number of proteinase inhibitors may be employed so long as they are not inhibitors of the proteinase used to release a foreign protein from the carrier protein. The practitioner will typically culture in a media or grow in an environment suitable for the host selected, prepare cell extract, then add appropriate cell protease inhibitors. The desired protein may be purified using standard procedures such as chromatography, electrophoresis or density gradient centrifugation.

The above methods are also applicable to purifying proteins from their native source.

Procedure for Purification of proteins that Form Inclusion bodies. U.S. Pat. No. 5,989,554 provides a general method for isolating and purifying proteins that form inclusion bodies in cells. First, the cells are lysed by enzymatic or mechanical means in a buffer. The preferred method is sonication, although any other lysis method will work, as long as lysis is complete and DNA and RNA are sufficiently fragmented so as not to pellet upon centrifugation. Preferred buffers contain Tris buffer at pH 7-8, isotonic saline, and dithiothreitol (DTT) to maintain all cell proteins in a reduced state. After sonication, detergent is added to the mixture to solubilize most lipids and proteins, and the mixture is centrifuged; it is preferred to use a centrifuge speed of greater than 10,000 g for 10 minutes. The desired protein is then found in the pellet fraction at a high degree of purity.

Higher purity is usually obtained by washing the pellet in a second wash solution, often containing a different agent or detergent. Washing is accomplished by resuspending the pellet in the fresh buffer followed by centrifugation as above. The preferred first detergent is sodium deoxycholate (Na-DOC), and the second preferred detergent is Triton X-100.

After the detergent washes, the pellet can be washed either with the above buffer or with phosphate-buffered saline (PBS) to remove trace detergent, then resuspended in a volume of a desired buffer for storage or use in any of the ways described elsewhere, including immunization.

The proteins purified by the above method are ready for use in any or all of the applications contemplated in the invention, including but not limited to the following; immunization of animals, use as an adjuvant, coupling to other ligands, use as a protease inhibitor, immobilization on hydrophobic surfaces, use as an enzyme substrate, and use in peptide production after cleavage.

As discussed earlier, this method is labor-intensive and does not provide large quantities of active protein.

Novel Method for Purifying Proteins that Form Inclusion Bodies. The present invention is based on the development of a single-column purification method for preparing milligram quantities of >95% pure, active 27 kDa NIa proteinase. The method comprises the following steps:

a) obtaining cells expressing the polypeptide;
b) lysing the cells;
c) pelleting inclusion bodies by centrifugation of the lysed cells;
d) centrifuging the inclusion bodies;
e) solubilizing the inclusion bodies in buffer containing solubilization agent;
f) centrifuging the solubilized inclusion bodies to obtain a supernatant containing the polypeptide;
g) loading the supernatant over a single denaturing column;
h) collecting the proteinase; and
i) renaturing the collected polypeptide.

Preferably, the cells are lysed by incubating for 30 min at 4° C. in 50 mM Tris-Cl, pH 8.0, 300 mM NaCl, 500 µg/ml lysozyme, 200 µg/ml DNase I, and protease inhibitors (such as PMSF and leupeptin); followed by three freeze-thaw cycles; addition of Triton X-100 to a final concentration of 1%; and vortexing. Preferably, following lysis the inclusion bodies are pelleted by centrifugation at 10,000×g. Preferably, the inclusion bodies are then solubilized with 6 M GuHCl, 100 mM $NaH_2PO_4$ and 10 mM Tris-Cl, pH 8.0. Preferably, before loading on the denaturing column the solubilized inclusion bodies are centrifuged for 20 minutes at 15,000×g. Preferably, the denaturing column contains Ni-NTA (nicke-nitilotiacetic acid-agarose) Superflow resin (Qiagen). Preferably, the proteinase is eluted with 6 M urea, 100 mM $NaH_2PO_4$, and 10 mM Tris-Cl, pH 4.5, and the collected proteinase fraction is adjusted with 10 N NaOH to pH 8.5, and renatured during dialysis for 4-8 hours in storage buffer (100 mM Tris-Cl, pH 8.5, 500 mM NaCl, 10% Glycerol, 5 mM DTT, 0.5 mM EDTA). Preferably, as a final step, the dialyzed proteinase fraction is centrifuged for 30 minutes at 15,000×g at 4° C. to collect the supernatant containing the active renatured proteinase.

Other proteinase inhibitors, methods for lysing the cells, buffers, solubilizing agents, and methods of renaturing the purified protein are well known to the skilled artisan, and some are described in the previous sections of the specification. It is also pointed out that any host cell that expresses large quantities of the protein of interest in the form of inclusion bodies or any cell that endogenously expresses the protein in the form of inclusion bodies are useful for purifying large quantities of the protein of interest.

In a preferred embodiment, the protein to be isolated in large quantities is expressed in *E. coli* as a fusion protein comprising in addition to the protein, a proteinase cleavage site, and a fusion partner. Proteinase cleavage sites, as well as fusion partner or carrier protein, are well known to the skilled artisan and have been described in detail in other sections of the present specification. A preferred proteinase cleavage site is the site recognized by the 27 kDa NIa proteinase and the preferred carrier protein is six His tags. The histidines enables binding to the Ni-NTA column. The 27 kDa NIa proteinase, unlike other proteinases, exhibits high specificity, insensitivity to many proteinase inhibitors used in protein purification, and efficient cleavage under broad range of temperatures (Polayes et al., 1994). Moreover, the protein to be purified is easily separated from the carrier peptide and the 27kDa NIa proteinase.

In light of the foregoing general discussion, the specific examples presented below are illustrative only and are not intended to limit the scope of the invention. Other generic and specific configurations will be apparent to those persons skilled in the art.

EXAMPLES

Example 1

Cloning

A wild type 27 kDa NIa nucleic acid was generated by PCR using pTL-5495 (ATCC 45036) as the template, 5TEVP1: 5'-CAT CAG CGG GCC ATG GCT GAA AGC TTG TTT AAG-3' (SEQ ID NO: 2) as the 5' primer, and 3TEVH1: 5'-CTG ATG CAC GGA TCC TCA TTA ATG GTG ATG GTG ATG GTG CAA TTG CGA GTA GAC TAA TTC ACT CAT G-3'(SEQ ID NO: 3) as the 3' primer. This nucleic acid translates to a proteinase with a C-terminal $His_6$ tag. The mutant 27 kDa NIa nucleic acid was generated by sequential PCR reactions using pTL-5495 as the template for the first reaction with 5TEVP1 as the 5' primer and TEVPSN: 5'-GAG TTG AGT TGC TTC TTT GAC TGG CTG AAA GGG TTC TTC AGG TTT GTT CAT GAA AAC TTT GTG GCC-3' (SEQ ID NO: 4) as the 3' primer to introduce the S219N mutation at the internal self-cleavage site. The resultant PCR product was used as the template in a second PCR reaction using the 5' primer 5TEVP1 and the 3' primer 3TEVH1. The nucleic acids were ligated into the pET15b expression vector (Novagen) using the NcoI and BamHI sites and transformed into E. coli DH5a (GibcoBRL) competent cells. Plasmids, pTPWT (wild type 27 kDa NIa proteinase) and pTPSN (mutant form with Ser to Asn mutation), were sequenced for accuracy and transformed into BL21 (DE3) (Novagen) competent cells for expression.

Example 2

Proteinase Expression and Purification

The wild-type and mutant form 27 kla NIa proteinases were expressed in BL21 (DE3) cells grown at 37° C. in Luria Broth with 100 μM Ampicillin to optical density 600>0.7. Cultures were induced with 400 μM IPTG for >4 hours. Cell pellets were harvested by centrifugation, resuspended in 50 ml buffer containing 50 mM Tris-Cl, pH 8.0 and 300 mM NaCl per liter of cell culture, and stored at −80° C. Lysis and purification of the soluble fraction containing the 27 kDa NIa proteinase were performed as described by Parks et al. (1995) through the Ni-NTA agarose purification step, except 10% glycerol, 300 mM NaCl, and 5 mM βME were included in all buffers, and the Ni-NTA agarose column was washed with buffer containing 10 mM imidazole and eluted with buffer containing 400 mM imidazole.

For inclusion body purification, cell suspensions were thawed in cool water and the buffer was adjusted to give a final concentration of 500 μg/ml lysozyme (Sigma), 200 μg/ml DNASE I (Boehringer Mannheim), 50 μg/ml PMSF, 10 μg/ml Leupeptin (Boehringer Mannheim), 20 mM $MgSO_4$, and 2 mM $CaCl_2$. The cells were lysed as follows: rocking for 30 minutes at 4° C., followed by 3 freeze-thaw cycles, lysed the cells; adding Triton x-100 to a final concentration of 1%; and vortexing. The inclusion bodies were pelleted by centrifugation at 10,000×g. Purified inclusion bodies were solubilized in a buffer containing 6 M GuHCl, 100 mM $NaH_2PO_4$ and 10 mM Tris-Cl, pH 8.0, and stored at −80° C.

Denaturing column chromatography was done at 4° C. using 10 ml Ni-NTA Superflow resin (Qiagen) per liter cell culture. The column was equilibrated with 10 column volumes (cv) of equilibration buffer (6M Urea, 100 mM $NaH_2PO_4$, and 10 mM Tris-Cl, pH 8.0). The solubilized inclusion bodies were thawed in a 65° C. bath and centrifuged 20 minutes at 15,000×g at 4° C. The supernatant was loaded onto the column by gravity flow. The column was washed with 4 cv equilibration buffer, then 6 cv wash buffer (6 M Urea, 100 mM $NaH_2PO_4$, and 10 mM Tris-Cl, pH 6.3). The proteinase was eluted in elution buffer (6 M Urea, 100 mM $NaH_2PO_4$, and 10 mM Tris-Cl, pH 4.5) with a 5 minute column incubation between each fraction until a total of 6 fractions were collected. Fractions containing the 27 kDa NIa proteinase were pooled, adjusted to pH 8.5 with 10 N NaOH, dialyzed 4-8 hours in storage buffer (100 mM Tris-Cl, pH 8.5, 500 mM NaCl, 10% Glycerol, 5 mM DTT, and 0.5 mM EDTA), and centrifuged 30 minutes at 15,000×g at 4° C. The supernatant, containing active, renatured 27 kDa Na proteinase was separated from the pellet, containing precipitated 27 kDa Na proteinase, and both were stored at −80° C. The pellet is successively resuspended in Equilibration Buffer and redialyzed to obtain more renatured, active proteinase as needed.

The 27 kDa NIa proteinase preparations were quantitated using the Bradford Assay (Biorad) using BSA as a standard. The yield of active 27 kDa NIa proteinase from the soluble preparation was estimated to be less than 10% of the total protein as this sample was not assayed for activity. For the insoluble preparation, the active 27 kDa NIa yield is reported as milligrams of proteinase obtained from the first renaturation of the eluate from the Ni-NTA agarose column.

Example 3

Activity Assays

A 17 kDa substrate containing the target cleavage site Glu-Asn-Leu-Tyr-Phe-Gln-Gly (SEQ ID NO: 5) produces a ~15 kDa peptide when cleaved with commercially available 27 kDa NIa proteinase (GibcoBRL). Substrate cleavage activity was assayed in 30 μl reactions with 100, 250, or 500 μM substrate and 0.75 μg proteinase in assay buffer (50 mM Tris-Cl, pH 8.0, 1 mM DTT, and 0.5 mM EDTA) incubated at 30° C. for 1 hour. Samples were electrophoresed in 15% SDS-PAGE gels, stained with Coomassie Blue, and protein bands were quantitated using a gel documentation system (Kodak). The net intensities of full-length and cleaved substrate bands were used to calculate the specific activity for the substrate at each substrate concentration.

Self-cleavage activity was assayed in 40 μl reactions containing 7.5 μg 27 kDa NIa proteinase in 50 mM Tris-Cl, pH 8.0, 1 mM DTT, and 0.5 mM EDTA, incubated at 4° C., −20° C., and −80° C. At 0.5, 1, 2, and 5.5 weeks, 10 μl sample was removed and boiled with denaturing SDS-PAGE loading buffer, loaded onto 15% SDS-PAGE gels, and quantitated as per above. The net intensities of full-length and cleaved proteinase bands were used to calculate the percent proteinase cleaved at each time point.

Results pTPWT and pTPSN encode peptides with respective molecular weights of 28,563 Daltons (about 28.5 kDa) and 28,590 Daltons (about 28.5kDa). During cloning, the proteinase N-terminus was altered from wild type Gly-Glu-Ser- to Met-Ala-Glu-Ser-(SEQ ID NO: 6) and a -Leu-His-His-His-His-His-His (SEQ ID NO: 7) tag was added to the C-terminus.

Soluble preparations of 27 kDa NIa proteinase yielded minimal quantities of proteinase (Table 1). 27 kDa NIa proteinase detected as a band in cell lysate is missing in clarified lysate but present in the inclusion body preparation (FIG. 1, lanes 1-3 and 7-9). Ni-NTA agarose purification under denaturing conditions yields purer proteinase than purification under soluble conditions (FIG. 1, lanes 4, 5, 10, and 11). In samples containing 4.5 μg total protein, a single contaminant is detected in renatured 27 kDa NIa proteinase after the denaturing purification indicating >95% purity (FIG. 1, lanes 13-15). Final yields of >10 mg renatured, active 27 kDa NIa proteinase were regularly obtained after a single renaturation step for both TPWT and TPSN (Table 1). Final concentrations of several renatured preps indicate a maximum solubility of ~1.5 mg/ml (data not shown).

TABLE 1

Purification Yields for Soluble vs Insoluble Procedures (per liter cell culture).

| | | Total protein Ni-NTA load (mg) | Total Ni-NTA-pure protein (mg) | active rTEVP (mg)* | % yield** |
|---|---|---|---|---|---|
| TPWT | Soluble prep | 977 | 4.08 | <0.41 | 0.04 |
| | Insoluble prep | 80 | 30.29 | >10.96 | 1.04 |
| TPSN | Soluble prep | 946 | 3.67 | <0.37 | 0.04 |
| | Insoluble prep | 81 | 32.35 | >12.84 | 1.25 |

*Active rTEVP for the soluble preps are estimated to be <10% of total purified protein. Data reported for insoluble preps is reported as greater than the quantity of protein obtained from a single round of renaturation.
**% yield active rTEVP from total cellular protein
Note:
Yields of total protein, active 27 kDa NIa proteinase, and overall percent yield are shown for both the soluble and insoluble purification protocols.
Protein quantitation at each purification step was estimated using the Bradford assay with a BSA standard curve.

Figure 2:
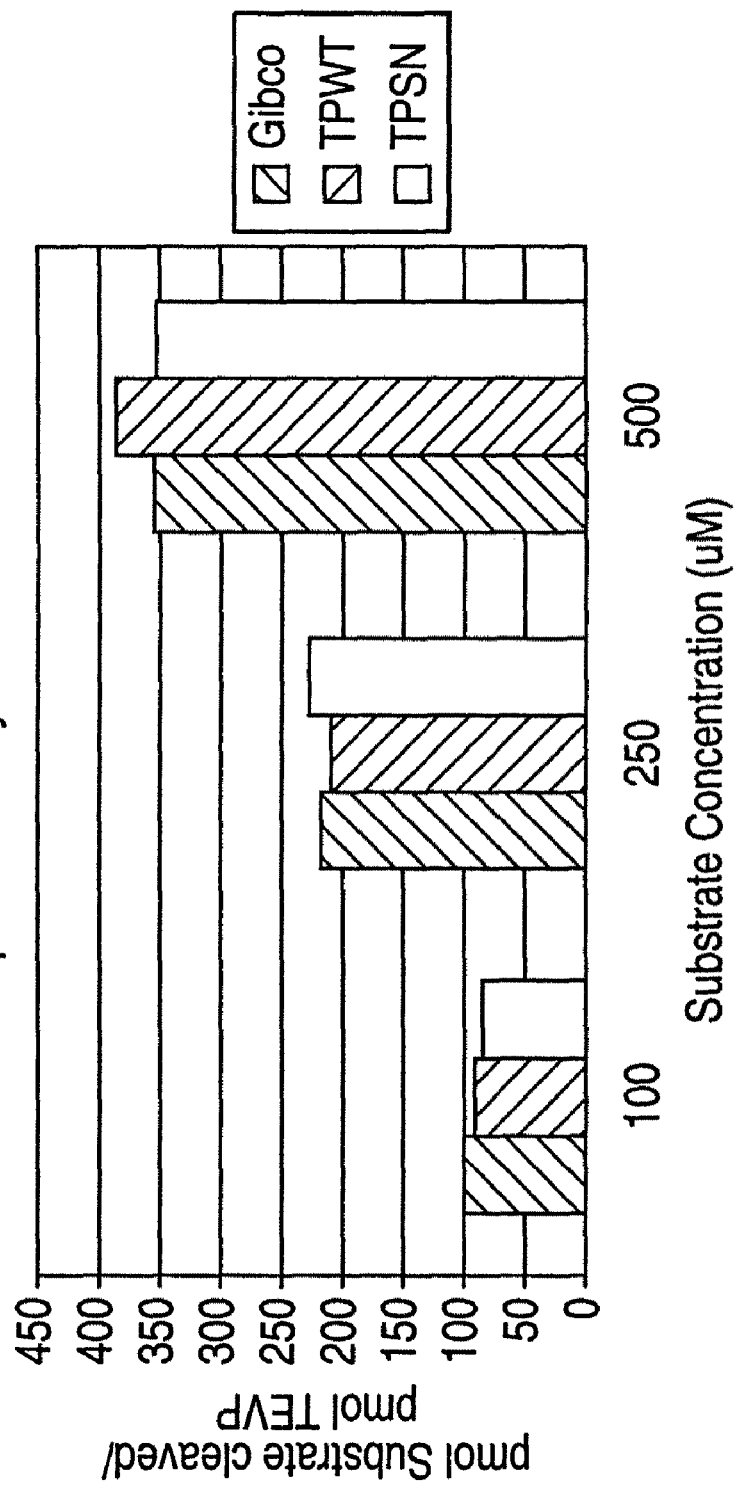
FIG. 2 shows specific activity for substrate cleavage by 27 kDa NIa proteinase. Specific activity is defined as picomoles substrate cleaved per picomole 27 kDa NIa proteinase in 1 hour at 30° C. TPWT and TPSN were compared to a commercially available 27 kDa NIa proteinase (GibcoBRL) at several substrate concentrations. The specific activity appears to be comparable for all samples at the substrate concentrations tested.

The specific activity for substrate cleavage is defined as the picomole substrate cleaved per picomole 27 kDa NIa proteinase in 1 hour at 30° C. The data indicate that TPWT and TPSN have similar activity to each other and to the commercially available proteinase at all substrate concentrations tested (FIG. 2).

Figure 3:
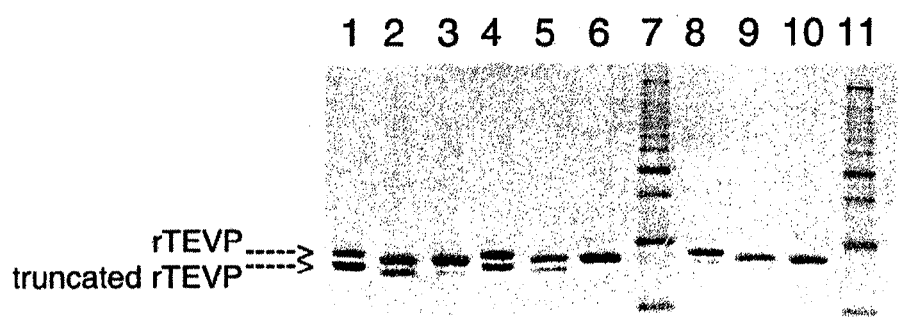
FIG. 3 shows self-cleavage of 27 kDa NIa proteinase after a 5.5 week incubation. TPWT, TPSN, and a commercially available 27 kDa NIa proteinase (GibcoBRL) were incubated at various temperatures for 5.5 weeks at a concentration of approximately 187.5 g proteinase/ml (micrograms proteinase/ml) reaction. Comparison of the 4° C. and −20° C. truncated 27 kDa NIa proteinase bands to those in the −80° C. samples indicates that self-cleavage activity is present in all samples at 4° C., but is absent from the TPSN sample at −20° C.
Figure 4A:
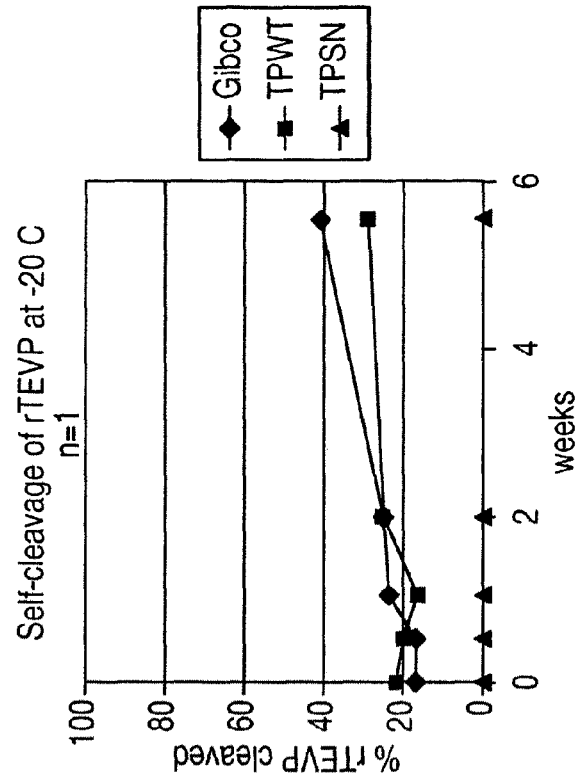
FIGS. 4A and 4B show self-cleavage of 27 kDa NIa proteinase at 4° C. and −20° C. TPWT, TPSN, and a commercially available 27 kDa NIa proteinase (GibcoBRL) were incubated at various temperatures for 5.5 weeks. Aliquots removed at the timepoints shown were run on SDS-PAGE gels and quantitated using a gel documentation system. Data were reported as the percent intensity of the truncated 27 kDa NIa proteinase band compared to the total intensity of both the full-length and truncated bands. The graphs show that TPWT has comparable self-cleavage activity to the commercially available 27 kDa NIa proteinase (assumed to have a wild type self-cleavage site) at both 4° C. and −20° C., while TPSN has reduced self-cleavage activity at 4° C. and no self-cleavage activity at −20° C.
Figure 4B:
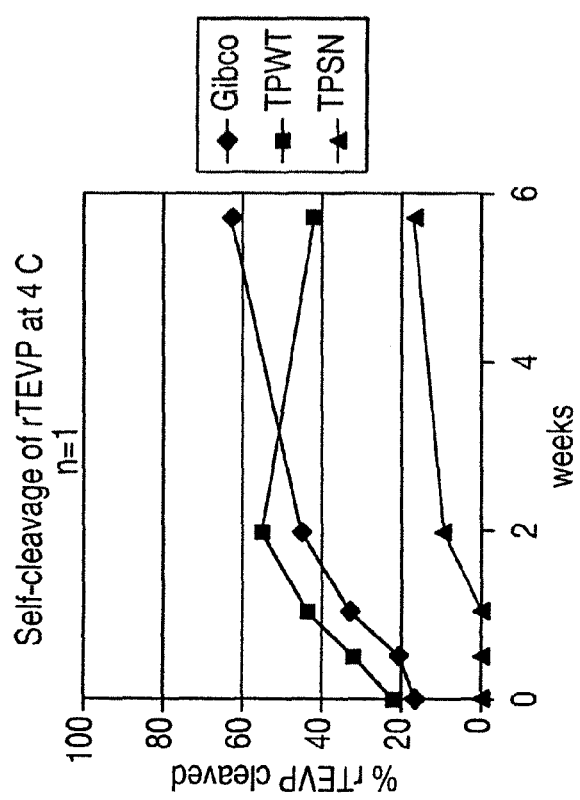

Both the commercially available 27 kDa NIa proteinase and purified TPWT contain the truncated self-cleavage product in the final preparation, while the TPSN preparation contains only full-length proteinase (FIG. 1, lanes 13-15). The self-cleavage activity of TPWT is similar to the commercially available proteinase at 4° C. and −20° C. TPSN has reduced self-cleavage activity at 4° C., and no self-cleavage activity at −20° C. (FIGS. 3, 4a, and 4b). None of the proteinase samples tested exhibited significant self-cleavage activity at −80° C. during our 5.5 week assay (data not shown).

Conclusions

The present invention shows that wild type, as well as mutant, histidine-tagged 27 kDa NIa constructs can be induced to express >95% of the proteinase in the insoluble fraction (FIG. 1). The present invention provides a novel method of denaturing purification of the insoluble fraction followed by renaturation of the peptide that yields up to 10 times as much active 27 kDa NIa proteinase as the soluble preparation reported by Parks et al (1995). This allows for stock preparations of >95% pure, active 27 kDa NIa proteinase to be made for general use.

Parks et al. (1995) has shown that the truncated form of 27 kDa NIa proteinase has significantly less substrate cleavage activity than the full-length form. The proteinase continues to cleave itself over time when stored at 4° C. and −20° C., potentially reducing the quantity of fully active enzyme in an 27 kDa NIa proteinase stock over time. Self-cleavage appears to be arrested at −80° C.

The Ser219→Asn mutation in the mutant form of the 27 kDa Ma proteinase, provided by the present invention, significantly inhibits self-cleavage activity, allowing for increased yields of full-length, fully active 27 kDa NIa proteinase, from either soluble or insoluble preps. The present invention also permits long-term storage of 27 kDa NIa stocks at −20° C., and short-term storage at 4° C.

The 27 kDa proteinase and its mutant form are valuable tools for protein purification protocols because of its target site specificity and its activity under a wide variety of conditions. The present invention by utilizing a denaturing preparation of the TPSN mutant, enables production of large stocks of rTEVP with consistent activity characteristics.

It should be understood that the foregoing discussion and examples merely present a detailed description of certain preferred embodiments. It therefore should be apparent to those of ordinary skill in the art that various modifications and equivalents can be made without departing from the spirit and scope of the invention. All journal articles, other references, patents, and patent applications that are identified in this patent application are incorporated by reference in their entirety.

REFERENCES

Allison, R., Johnston, R. E., and Dougherty, W. G. (1986) The Nucleotide Sequence of the Coding Region of the Tobacco Etch Virus Genomic RNA: Evidence for the Synthesis of a Single Polyprotein. *Virology* 154, 9-20

Argos, P., Kamer, P., Nicklin, M. J. H., and Wimmer, E. (1984). Similarity in gene organization and homology between proteins of animal picornaviruses and plant comoviruses suggest common ancestry of these virus families. *Nucleic Acids Res.* 12, 7251-7267.

Bazan, J. F., and Fletterick, R. J. (1990). Structural and catalytic models of trypsin-like viral proteases. *Semin. Virol.* 1, 311-322.

Carrington, J. C. and Dougherty, W. G. (1988) A Viral Cleavage Site Cassette: Identification of Amino Acid Sequences Required for Tobacco Etch Virus Polyprotein Processing. *Biochem* 85, 3391-3395

Carrington, J. C., Cary, S. M., Parks, T. D., and Dougherty, W. B. (1989) A Second Proteinase Encoded by a Plant Potyvirus Genome. *EMBO J.* 8, 365-370

Dougherty, W. G., Parks T. D., Cary, S. M, Bazan, J. F. and Fletterick, R. J. (1989b). Characterization of the catalytic residues of the tobacco etch virus 49-kDa proteinase. *Virology* 172, 302-310.

Dougherty, W. G., Cary, S. M. and Parks T. D. (1989a). Molecular genetic analysis of a plant virus polyprotein cleavage site: A model. *Virology* 171, 356-364.

Dougherty, W. G., and Parks T. D. (1989). Molecular genetic and bio-chemical evidence for the involvement of the heptapeptide cleavage sequence in determining the reaction profile at two tobacco etch virus cleavage sites in cell-free assays. *Virology* 172, 145-155.

Dougherty, W. G., and Parks T. D. (1991). Post-translational processing of the tobacco etch virus 49-kDa small nuclear inclusion polyprotein: Identification of an internal cleavage site and delimitation of Vpg and proteinase domains. *Virology* 183, 449-456.

Dougherty, W. G. and Hiebert, E. (1980) Translation of Potyvirus RNA in a Rabbit Reticulocyte Lysate: Identification of Nuclear Inclusion Proteins as Products of Tobacco Etch Virus RNA Translation and Cylindrical Inclusion Protein as a Product of the Potyvirus Genome. *Vir* 104, 174-182

Dougherty, W. G. and Parks, T. D. (1989a) Molecular Genetic and Biochemical Evidence for the Involvement of the Heptapeptide Cleavage Sequence in Determining the Reaction Profile at Two Tobacco Etch Virus Cleavage Sites in Cell-Free Assays. *Vir* 172, 145-155

Dougherty, W. G., Carrington, J. C., Cary, S. M., and Parks, T. D. (1988) Biochemical and Mutational Analysis of a Plant Virus Polyprotein Cleavage Site. *EMBO* 7, 1281-1287

Dougherty, W. G., Cary, S. M., and Parks, T. D. (1989b) Molecular Genetic Analysis of a Plant Virus Polyprotein Cleavage Site: A Model. *Vir* 171, 356-364

Krausslich, H. G., and Wimmer, E. (1988). Viral Proteinases. *Annu. Rev. Biochem.* 57, 701-754.

Lawson, M. A. and Semler, B. L, (1990) Picornavirus Protein Processing: Enzymes, Substrates, and Genetic Regulation. Curr. Topics Micro. Immun. 161: 49-87

Lawson, M. A. and Semler, B. L. (1991) Alternate Poliovirus Non-Structural Protein Processing Cascades Generated by Primary Sites of 3C Proteinase Cleavage. Virology 191: 309-320

Parks, T. D., Howard, E. D., Wolpert, T. J., Arp, D. J., and Dougherty, W. G. (1995) Expression and Purification of a Recombinant Tobacco Etch Virus Nia Proteinase: Biochemical Analyses of the Full-Length and a Naturally Occurring Truncated Proteinase Form. *Vir* 210, 194-201

Parks, T. D., Leuther, K. K., Howard, E. D., Johnston, S. A., and Dougherty, W. G. (1994) Release of Proteins and Peptides from Fusion Proteins Using a Recombinant Plant Virus Proteinase. *Anal. Biochem.* 216, 413-417

Polayes, D. A., Goldstein, A., Ward G., and Hughes, A. J. Jr. (1994) TEV Protease, Recombinant: A Site-Specific Protease for Efficient Cleavage of Affinity Tags from Expressed Proteins in "Focus" 16, #1, Life Technologies, Inc.

Taylor and Drickamer (1991) Carbohydrate-Recognition Domains as Tools for Rapid Purification of Recombinant Eukaryotic Proteins. *Biochemistry Journal* 99, 243-248

Verchot, J., Koonin, E. V., and Carrington, J. C. (1991) The 35 kDaProtein from the N-terminus of the Potyiral Polyprotein Functions as a Third Virus-Encoded Proteinase. *Virology* 185, 60-69

---

The invention claimed is:

1. An isolated active mutant tobacco etch virus (TEV) proteinase having a single amino acid change in the internal self-cleavage site, wherein the active mutant TEV proteinase has the same substrate activity relative to the substrate activity of wild-type TEV proteinase, and wherein the single amino acid change in the internal self cleavage site is at the residue corresponding to Ser 219 of the wild-type TEV proteinase.

2. The isolated active mutant TEV proteinase of claim 1, wherein the active mutant TEV proteinase has an Asn residue at the residue corresponding to Ser 219 of the wild-type TEV proteinase.

* * * * *